(12) United States Patent
Reyes et al.

(10) Patent No.: US 11,376,419 B2
(45) Date of Patent: Jul. 5, 2022

(54) DYNAMIC HQ FOR CLOSED LOOP CONTROL

(71) Applicant: HeartWare, Inc., Miami Lakes, FL (US)

(72) Inventors: Carlos Reyes, Davie, FL (US); Fernando Casas, Miami Lakes, FL (US)

(73) Assignee: HEARTWARE, INC., Miami Lakes, FL (US)

( * ) Notice: Subject to any disclaimer, the term of this patent is extended or adjusted under 35 U.S.C. 154(b) by 36 days.

(21) Appl. No.: 17/017,873

(22) Filed: Sep. 11, 2020

(65) Prior Publication Data

US 2020/0405931 A1 Dec. 31, 2020

Related U.S. Application Data

(62) Division of application No. 16/148,312, filed on Oct. 1, 2018, now Pat. No. 10,806,840.

(Continued)

(51) Int. Cl.
*A61M 60/50* (2021.01)
*A61M 60/148* (2021.01)
(Continued)

(52) U.S. Cl.
CPC .......... *A61M 60/50* (2021.01); *A61M 60/148* (2021.01); *A61M 60/419* (2021.01);
(Continued)

(58) Field of Classification Search
CPC .. A61M 60/50; A61M 60/148; A61M 60/419; A61M 60/857; A61M 2205/3331; A61M 2205/3334; A61M 2205/3365
See application file for complete search history.

(56) References Cited

U.S. PATENT DOCUMENTS

| 6,688,861 | B2 | 2/2004 | Wampler |
| 7,575,423 | B2 | 8/2009 | Wampler |

(Continued)

FOREIGN PATENT DOCUMENTS

WO 2011163360 A1 12/2011

OTHER PUBLICATIONS

International Search Report and Written Opinion dated Jan. 21, 2019, for corresponding International Application No. PCT/2018/053713; International Filing Date: Oct. 1, 2018 consisting of 10-pages.

*Primary Examiner* — Paula J Stice

(74) *Attorney, Agent, or Firm* — Shumaker & Sieffert, P.A.

(57) ABSTRACT

A method of controlling a blood pump having a predefined hydraulic performance including at least from the group consisting of estimating and measuring an instantaneous flow rate during operation of the blood pump at a predetermined rotational speed of an impeller of the blood pump, the instantaneous flow rate including a plurality of flow rate data points. The plurality of flow rate data points define a trajectory around at least one from the group consisting of an operational point of a predefined pressure-flow curve associated with the predetermined rotational speed of the impeller of the blood pump and a target operational point of a target pressure-flow curve different than the predefined pressure-flow curve. The predetermined rotational speed of the impeller is adjusted until the plurality of flow rate data points define a predetermined trajectory around at least one of the operational point and the target operational point.

9 Claims, 3 Drawing Sheets

Related U.S. Application Data

(60) Provisional application No. 62/571,964, filed on Oct. 13, 2017.

(51) Int. Cl.
*A61M 60/419* (2021.01)
*A61M 60/857* (2021.01)

(52) U.S. Cl.
CPC ... *A61M 60/857* (2021.01); *A61M 2205/3331* (2013.01); *A61M 2205/3334* (2013.01); *A61M 2205/3365* (2013.01)

(56) References Cited

U.S. PATENT DOCUMENTS

| | | |
|---|---|---|
| 7,976,271 B2 | 7/2011 | LaRose et al. |
| 8,007,254 B2 | 8/2011 | LaRose et al. |
| 8,419,609 B2 | 4/2013 | Shambaugh, Jr. et al. |
| 8,897,873 B2 | 11/2014 | Schima et al. |
| 8,961,390 B2 | 2/2015 | LaRose et al. |
| 9,511,179 B2 | 12/2016 | Casas et al. |
| 2011/0313517 A1 | 12/2011 | Reichenbach et al. |
| 2015/0051438 A1 | 2/2015 | Taskin |
| 2015/0283312 A1 | 10/2015 | Reichenbach et al. |
| 2017/0326282 A1 | 11/2017 | Wilt et al. |
| 2018/0028738 A1 | 2/2018 | Brown et al. |

DYNAMIC HQ FOR CLOSED LOOP CONTROL

CROSS-REFERENCE TO RELATED APPLICATION

This application is a divisional of U.S. application Ser. No. 16/148,312, filed Oct. 1, 2018, and issued as U.S. Pat. No. 10,806,840 on Oct. 20, 2020, which claims the benefit of U.S. Application Ser. No. 62/571,964, filed Oct. 13, 2017.

FIELD

The present technology relates to a method for automating speed changes in a rotary blood pump to produce a desired pressure-flow relationship.

BACKGROUND

Rotary blood pumps have inherent hydraulic performance that is unique to the design of each pump. This performance is summarized by a pump's pressure vs. flow (HQ) curves, a series of curves, which vary by pump speed. An exemplary HQ for the HVAD® pump (FIG. 1) sold by HeartWare, Inc. is shown in FIG. 2. The behavior of a pump in a steady-state or pulsatile environment will depend on the shape and values of these curves. However, clinicians and physicians may be desirous of a particular HQ curve different than the inherent HQ curve of the pump depending on, among other things, the patient's needs and associated adverse events. For example, as shown in FIG. 2, an exemplary target HQ curve is shown superimposed on the inherent HQ curves of the HVAD pump. Prior approaches to achieve a target HQ response would be by a guess and check methodology. This would require a manual speed adjustment and wait for a settling of physiological parameters such as pressure and flow. This is done using averaged parameters and cannot be translated to an instantaneous or real-time application.

SUMMARY

The techniques of this disclosure generally relate to a system and method for automating speed changes in a rotary blood pump to produce a desired pressure-flow relationship.

In one aspect, the present disclosure provides for a method of controlling an implantable blood pump having a predefined hydraulic performance. The method includes at least from the group consisting of estimating and measuring an instantaneous flow rate during operation of the blood pump at a predetermined rotational speed of an impeller of the blood pump, the instantaneous flow rate including a plurality of flow rate data points. The plurality of flow rate data points define a trajectory around at least one from the group consisting of an operational point of a predefined pressure-flow curve associated with the predetermined rotational speed of the impeller of the blood pump and a target operational point of a target pressure-flow curve different than the predefined pressure-flow curve. The predetermined rotational speed of the impeller is adjusted until the plurality of flow rate data points define a predetermined trajectory around at least one of the operational point and the target operational point.

In another aspect, the disclosure provides for estimating an average flow rate during operation of the blood pump at the predetermined rotational speed and adjusting the predetermined rotational speed of the impeller of the implantable blood pump until the estimated average flow rate is substantially equal to a target average flow rate.

In another aspect, the disclosure provides for correlating the trajectory of the plurality of flow rate data points to a pump preload sensitivity.

In another aspect, the disclosure provides for correlating the trajectory of the plurality of flow rate data points to a pump condition resistant to high pressure conditions.

In another aspect, the disclosure provides for correlating the trajectory of the plurality of flow rate data points to a pump condition resistant to retrograde flow.

In another aspect, the disclosure provides that the instantaneous flow rate is estimated.

In another aspect, the disclosure provides that the instantaneous flow rate is measured.

In another aspect, the disclosure provides that the plurality of flow rate data points define the trajectory around the operational point of the predefined pressure-flow curve associated with the predetermined rotational speed of the impeller of the blood pump.

In another aspect, the disclosure provides that the plurality of flow rate data points define the target operational point of the target pressure-flow curve different than the predefined pressure-flow curve.

In one aspect, the disclosure provides for a system for controlling an implantable blood pump having a predefined hydraulic performance. The system includes a controller in communication with the implantable blood pump, the implantable blood pump having an impeller, the controller being configured to at least from the group consisting of estimate and measure an instantaneous flow rate during operation of the blood pump at a predetermined rotational speed of an impeller of the blood pump, the instantaneous flow rate including a plurality of flow rate data points. The plurality of flow rate data points define a trajectory around at least one from the group consisting of an operational point of a predefined pressure-flow curve associated with the predetermined rotational speed of the impeller of the blood pump and a target operational point of a target pressure-flow curve different than the predefined pressure-flow curve. The controller is further configured to adjust the predetermined rotational speed of the impeller until the plurality of flow rate data points define a predetermined trajectory around at least one of the operational point and the target operational point.

In another aspect, the disclosure provides that the implantable blood pump includes a flow meter downstream from the impeller, and wherein the controller is configured to measure the instantaneous flow rate.

In another aspect, the disclosure provides that the instantaneous flow rate is estimated.

In another aspect, the disclosure provides that the controller is further configured to estimate an average flow rate during operation of the blood pump at the predetermined rotational speed and adjust the predetermined rotational speed of an impeller of the implantable blood pump until the estimated average flow rate is substantially equal to a target average flow rate.

In another aspect, the disclosure provides that the controller is further configured to correlate the trajectory of the plurality of flow rate data points to a pump preload sensitivity.

In another aspect, the disclosure provides that the controller is further configured to correlate the trajectory of the plurality of flow rate data points to a pump condition resistant to high pressure conditions.

In another aspect, the disclosure provides that the controller is further configured to correlate the trajectory of the plurality of flow rate data points to a pump condition resistant to retrograde flow.

In another aspect, the disclosure provides that the instantaneous flow rate is measured.

In another aspect, the disclosure provides that the plurality of flow rate data points define the trajectory around the operational point of the predefined pressure-flow curve associated with the predetermined rotational speed of the impeller of the blood pump.

In another aspect, the disclosure provides that the plurality of flow rate data points define the target operational point of the target pressure-flow curve different than the predefined pressure-flow curve.

In one aspect, the disclosure provides for a system for controlling an implantable blood pump having a predefined hydraulic performance. The system includes a controller in communication with the implantable blood pump, the implantable blood pump having an impeller, the controller being configured to at least from the group consisting of estimate and measure an instantaneous flow rate during operation of the blood pump at a predetermined rotational speed of an impeller of the blood pump, the instantaneous flow rate including a plurality of flow rate data points. The plurality of flow rate data points define a trajectory around at least one from the group consisting of an operational point of a predefined pressure-flow curve associated with the predetermined rotational speed of the impeller of the blood pump and a target operational point of a target pressure-flow curve different than the predefined pressure-flow curve. The controller further correlates the trajectory of the plurality of flow rate data points to a pump condition resistant to high pressure conditions and adjusts the predetermined rotational speed of the impeller until the plurality of flow rate data points define a predetermined trajectory around at least one of the operational point and the target operational point. The controller further estimates an average flow rate during operation of the blood pump at the predetermined rotational speed and adjusts the predetermined rotational speed of an impeller until the estimated average flow rate is substantially equal to a target average flow rate.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
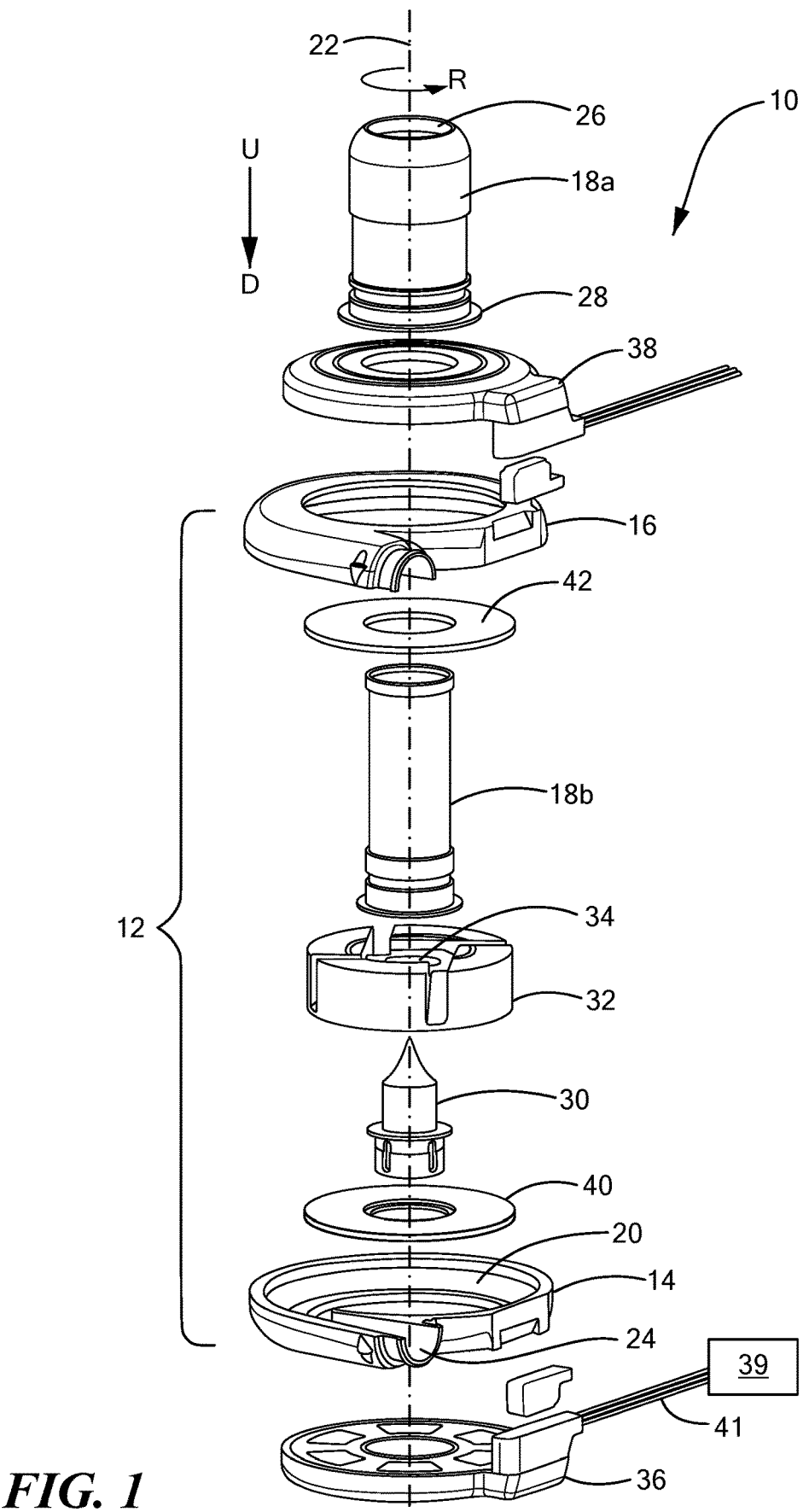
FIG. 1 is an exploded view showing an exemplary HVAD blood constructed in accordance with the principles of the present application.

Before describing in detail exemplary embodiments, it is noted that the embodiments reside primarily in combinations of apparatus components and processing steps related to method for automating speed changes in a rotary blood pump to produce a desired pressure-flow relationship. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Referring now to the drawings in which like reference designators refer to like elements there is shown in FIG. 1 an exemplary blood pump constructed in accordance with the principles of the present application and designated generally "10." The blood pump 10 according to one embodiment of the disclosure includes a static structure or housing 12 which houses the components of the blood pump 10. In one configuration, the housing 12 includes a lower housing or first portion 14, an upper housing or second portion 16, and an inlet portion or inflow cannula 18 which includes an outer tube 18a and an inner tube 18b. The first portion 14 and the second portion 16 cooperatively define a volute shaped chamber 20 having a major longitudinal axis 22 extending through the first portion and inflow cannula 18. The chamber 20 defines a radius that increases progressively around the axis 22 to an outlet location on the periphery of the chamber 20. The first portion 14 and the second portion 16 define an outlet 24 in communication with chamber 20. The first portion 14 and the second portion 16 also define isolated chambers (not shown) separated from the volute chamber 20 by magnetically permeable walls.

The inflow cannula 18a-18b ("18") is generally cylindrical and extends from first portion 14 and extends generally along axis 22. The inflow cannula 18 has an upstream end or proximal end 26 remote from second portion 16 and a downstream end or distal end 28 proximate the chamber 20. The parts of the housing 12 mentioned above are fixedly connected to one another so that the housing 12 as a whole defines a continuous enclosed flow path. The flow path extends from upstream end 26 at the upstream end of the flow path to the outlet 24 at the downstream end of the flow path. The upstream and downstream directions along the flow path are indicated by the arrows U and D respectively. A post 30 is mounted to first portion 14 along axis 22. A generally disc shaped ferromagnetic rotor 32, for example, and impeller with a central hole 34, is mounted within chamber 20 for rotation about the axis 22. Rotor 32 includes a permanent magnet and also includes flow channels for transferring blood from adjacent the center of the rotor 32 to the periphery of the rotor 32. In the assembled condition, post 30 is received in the central hole of the rotor 32. A first stator 36 having a plurality of coils may be disposed within the first portion 14 downstream from the rotor 32. The first stator 36 may be axially aligned with the rotor along axis 22 such that when a current is applied to the plurality of coils in the first stator 36, the electromagnetic forces generated by the first stator 36 rotate the rotor 32 and pump blood. A second stator 38 may be disposed within the second portion 16 upstream from the rotor 32. The second stator 38 may be configured to operate in conjunction with or independently of the first stator 36 to rotate the rotor 32.

An electrical connector 41 is provided on first portion 14 for connecting the coils to a source of power such as a controller 39. The controller 39 is arranged and configured to apply power to the coils of the pump to create a rotating magnetic field which spins rotor 32 around axis 22 in a predetermined first direction of rotation, such as the direction R indicated by the arrow in FIG. 1, i.e., counterclockwise as seen from the upstream end of inflow cannula 18. In other configurations of the blood pump 10, the first direction may be clockwise. Rotation of the rotor 32 impel blood downstream along the flow path so that the blood, moves in a downstream direction D along the flow path, and exits through the outlet 24. During rotation, hydrodynamic and magnetic bearings (not shown) support the rotor 32 and maintain the rotor 32 out of contact with the surfaces of the elements of the first portion 14 and the second portion 16 during operation. A first non-ferromagnetic disk 40 may be disposed within the first portion 14 downstream from the rotor 32 between the first stator 36 and the rotor 32 and a second non-ferromagnetic disk 42 may be disposed upstream from the rotor 32 within the second portion 16 between the second stator 38 and the rotor 32. The general arrangement of the components described above may be similar to the blood pump 10 used in the MCSD sold under the designation HVAD by HeartWare, Inc., assignee of the present application. The arrangement of components such as the magnets, electromagnetic coils, and hydrodynamic bearings used in such a pump and variants of the same general design are described in U.S. Pat. Nos. 6,688,861; 7,575,423; 7,976,271; and 8,419,609, the disclosures of which are hereby incorporated by reference herein. It is contemplated pumps having a single stator as described, for example, in U.S. Pat. No. 8,007,254 and U.S Patent Application Publication No. 2015/0051438 A1, sold under the designation MVAD by HeartWare, Inc., assignee of the present application, are contemplated to be used with method of the present application.

Figure 2:
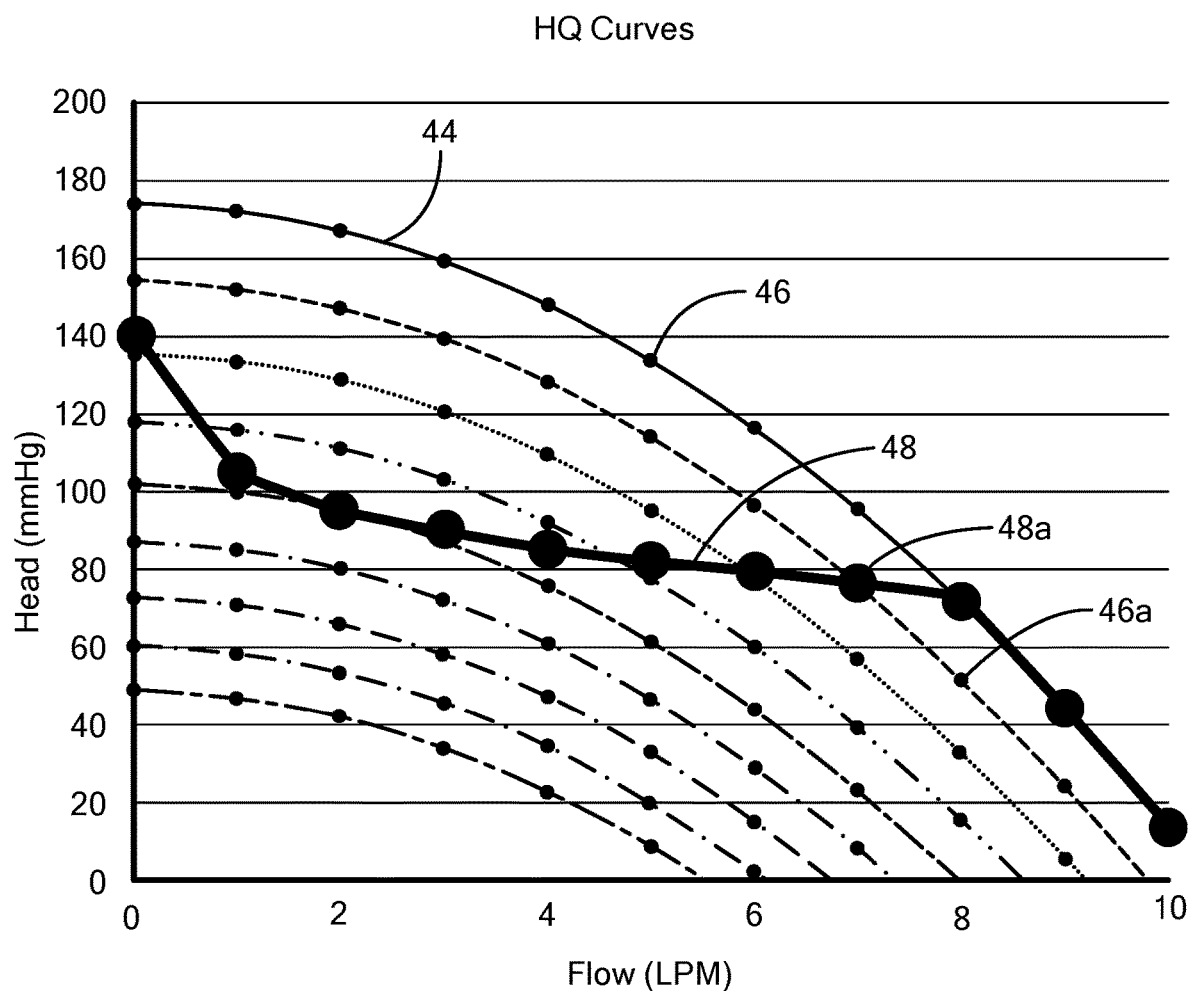
FIG. 2 is a graph showing predetermined pressure-flow ("HQ") curves associated with the HVAD pump and a target HQ curve superimposed on the predetermined HQ curves.

Referring now to FIG. 2, a plurality of predefined pressure-flow or HQ curves 44 are shown for the blood pump 10. The HQ curves 44 define a predefined pump hydraulic performance regardless of the rotational speed of the rotor or impeller 32 of the pump 10 when operating in closed loop. In other words, each curve of the HQ curves 44 represents the expected pressure-flow profile for a given constant speed of the impeller 32 and constant viscosity of the fluid flowing through the pump 10, for example, blood. The HQ curves 44 indicate that as flow increases from 0-10 LPM the pressure-head, i.e. the differential pressure between the pressure upstream of the inflow cannula 18 and downstream of the pump 10 at outlet 24, decreases. Operational points 46, indicated by bullets in FIG. 2, are average reference points to estimate or otherwise determine the average pressure-head and average flow at a given constant speed of the impeller 32 that is associated with the HQ curve 44. For example, as shown in FIG. 2, operational point 46a is expected to produce an average flow of about 8 LPM at an average pressure-head of about 50 mmHg. Thus, based on the predefined HQ curves, if the speed of the impeller 32 and the flow is known, the pressure-head may be calculated.

Continuing to refer to FIG. 2, a target HQ curve 48 represents a target HQ hydraulic performance different than the HQ curve 44 with target operational points 48a. For example, target operational point 48a is expected to produce an average flow of about 7 LM at an average pressure of about 80 mmHg, which is different than the predefined HQ curve at the given constant speed and viscosity. To achieve the target HQ curve 48, the controller 39 may modulate or otherwise adjust the speed of the impeller 32 to average speeds that results in the target HQ curve 48 and target operational point 48a.

Figure 3:
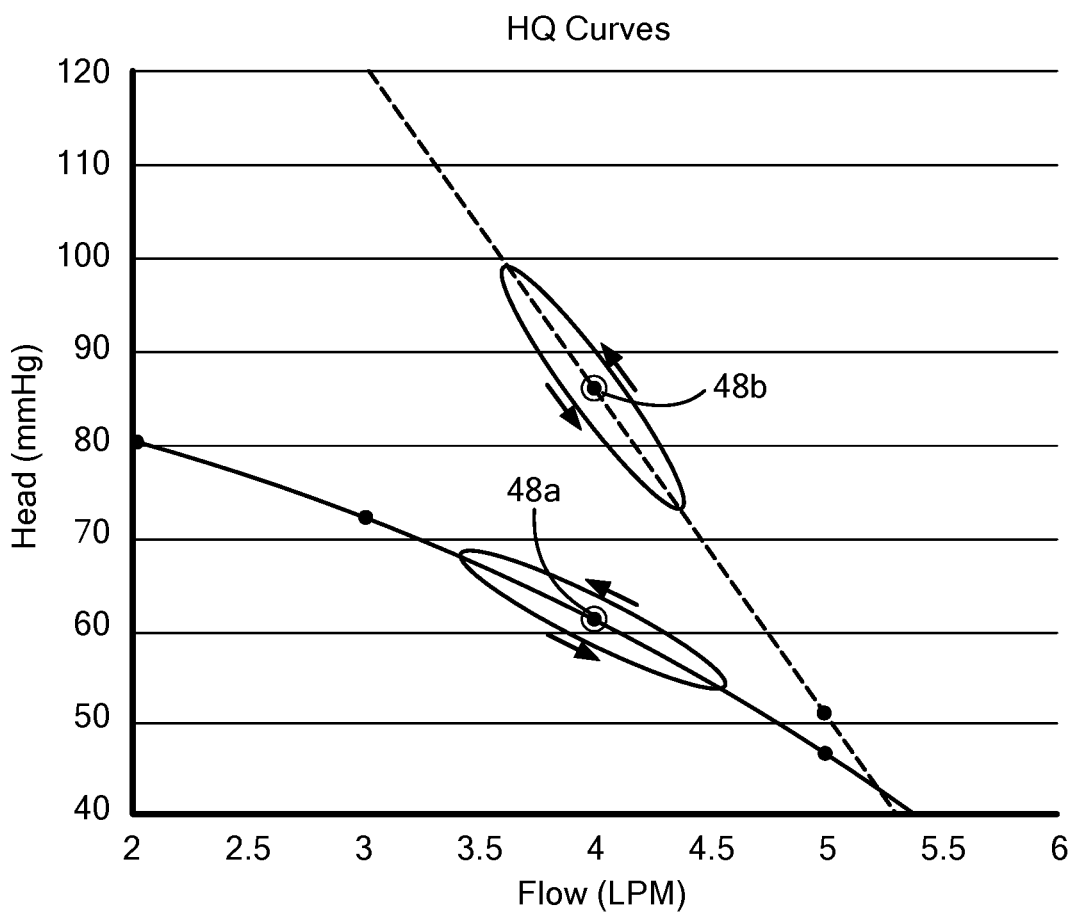
FIG. 3 is graph showing an operational point along a target HQ curve (solid line) and the trajectory (dashed line) of a plurality of flow rate data points around an operational point of a blood pump for a predetermined constant speed.

Referring now to FIG. 3, target HQ curve 48 is shown with a target operational point 48a. The elliptical orbit around target operational point 48a represents the instantaneous flow rate measurements or estimations made by the controller 39 to derive at the average operational point 48a. The instantaneous flow rate may be estimated by methods known in the art and may include, but are not limited to, the method of estimating flow in a blood pump disclosed in U.S. Pat. Nos. 8,897,873, 9,511,179, and 8,961,390, the entirety of which are incorporated herein by reference. Alternatively, instantaneous flow may be measured by including a flow meter downstream from outlet 24. The ellipse and arrows around the target operational point 48a indicate the boundary of the instantaneous flow rate estimations and/or measurements and the direction of the plurality of instantaneous flow points around the target operational point 48a. For example, it is expected that the instantaneous flow points fall within the ellipse and the average of those points establishes the target operational point 48a. The arrows indicate the direction of those instantaneous points to identify trends and those trends can be manipulated for each target operational point 48a.

Figure 4:
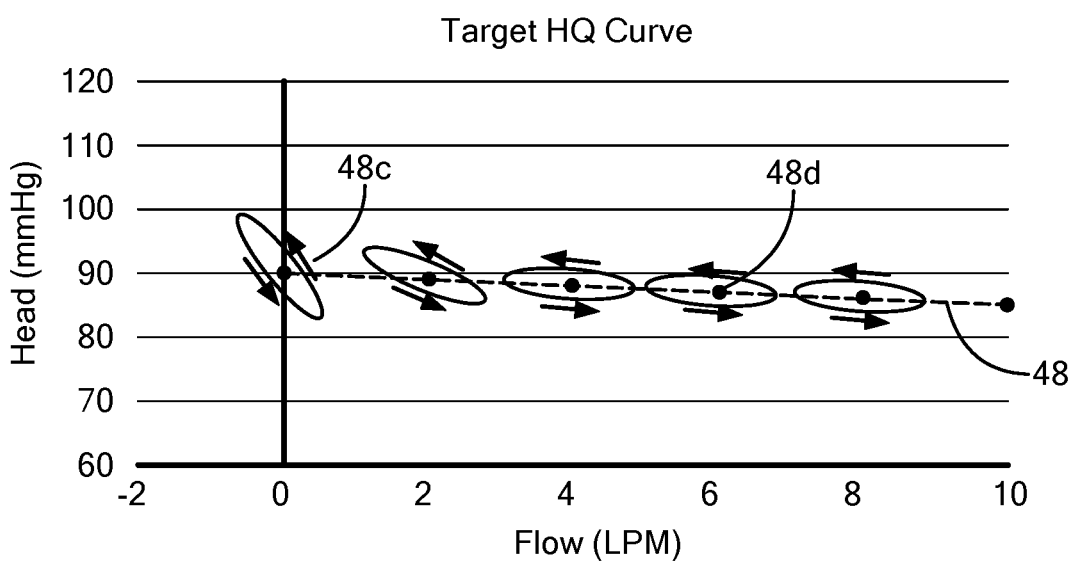
FIG. 4 is a graph showing a plurality of operational points along a target HQ curve and the trajectory (ellipses) of a plurality of flow rate data points around the associated operational point.

Referring now to FIGS. 3-4, the slope of the ellipse is indicative of a trajectory of the instantaneous points that comprise the average target operating point 48a. For example, as shown in FIG. 3, target operational point 48b defines an ellipse of instantaneous points that define and average represented by target operational point 48b. The trajectory of the ellipse defines a slope indicated by the dashed lines. The trajectory of the ellipse may be indicative of a pump characteristic and/or adverse events. For example, as shown in FIG. 4, the trajectory of the ellipse around lower flow regions, as shown with respect to target operational point 48c, may be an operational point that prevents high pressure conditions and prevent retrograde flow in the pump 10. A flatter ellipse trajectory, as shown associated with target operational point 48d may increase preload sensitivity. Thus, the target HQ curve 48 may have a number of target operational points 48a that may be tailored for desired conditions. In another words, the controller 39 may automatically adjust the rotational speed of the impeller 32 to create the desired trajectory of instantaneous flow points and also adjust the impeller 32 to operate at the average operational point along a target HQ curve 48. For example, the controller 39 slew rates may be modified to support the desired speed changes in the impeller 32. Similarly, the desired trajectory around an operational point 46 along HQ curve 44 may also be created by adjusting the predetermined speed of the impeller 32.

In an exemplary method of operation, the instantaneous flow is estimated or measured during operation of the blood pump at a predetermined rotational speed of an impeller 32 of the blood pump 10. For example, the flow may be measured while the impeller 32 is rotating at a speed of 2800 RPM, or alternatively when the pump is operating an impeller speed that creates a target HQ curve 48. The instantaneous flow rate includes a plurality of flow rate data points that define an ellipse around the average of those data points. The average of the instantaneous flow points define either a predefined operational point 46 associated with the predefined pressure-flow curve 44, or the rotational speed of the impeller 32 may have been adjusted to create a target operational point 48 that is not associated with the predefined pressure-flow curve. The predetermined rotational speed of the impeller 32 is adjusted until the plurality of flow rate data points define a predetermined trajectory around a target operating point 48 or the operational point 46. Thus, the method provides for operational point control whether the pump 10 is operating at an operational point 46 associated with the predefined pressure-flow curves, or when the pump 10 is operating at a target operational point 48a under a target pressure-flow curve 48. It is further contemplated that the above method is applicable not only when the pump 10 is operating under static conditions, but also under pulsatile conditions.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of controlling an implantable blood pump, the method comprising:
    estimating or measuring an instantaneous flow rate during operation of the blood pump at a predetermined rotational speed of an impeller of the blood pump, the instantaneous flow rate including a plurality of flow rate data points; the plurality of flow rate data points defining a trajectory around at least one from the group consisting of an operational point of a predefined pressure-flow curve associated with the predetermined rotational speed of the impeller of the blood pump and a target operational point of a target pressure-flow curve different than the predefined pressure-flow curve; and
    adjusting the predetermined rotational speed of the impeller until the plurality of flow rate data points define a predetermined trajectory around at least one of the operational point and the target operational point.

2. The method of claim 1, further comprising:
    estimating an average flow rate during operation of the blood pump at the predetermined rotational speed; and
    adjusting the predetermined rotational speed of the impeller of the implantable blood pump until the estimated average flow rate is at a target average flow rate.

3. The method of claim 1, further comprising correlating the trajectory of the plurality of flow rate data points to a pump preload sensitivity.

4. The method of claim 1, further comprising correlating the trajectory of the plurality of flow rate data points to a pump condition resistant to high pressure conditions.

5. The method of claim 1, further comprising correlating the trajectory of the plurality of flow rate data points to a pump condition resistant to retrograde flow.

6. The method of claim 1, wherein the instantaneous flow rate is estimated.

7. The method of claim 1, wherein the instantaneous flow rate is measured.

8. The method of claim 1, wherein the plurality of flow rate data points define the trajectory around the operational point of the predefined pressure-flow curve associated with the predetermined rotational speed of the impeller of the blood pump.

9. The method of claim 1, wherein the plurality of flow rate data points define the target operational point of the target pressure-flow curve different than the predefined pressure-flow curve.

* * * * *